(12) United States Patent
Gunn

(10) Patent No.: US 9,125,691 B2
(45) Date of Patent: Sep. 8, 2015

(54) TRANSVERSE CROSSLINK DEVICE

(75) Inventor: Joshua Gunn, Marietta, GA (US)

(73) Assignee: Amendia, Inc., Marietta, GA (US)

( * ) Notice: Subject to any disclaimer, the term of this patent is extended or adjusted under 35 U.S.C. 154(b) by 109 days.

(21) Appl. No.: 13/336,871

(22) Filed: Dec. 23, 2011

(65) Prior Publication Data

US 2013/0165976 A1 Jun. 27, 2013

(51) Int. Cl.
*A61B 17/88* (2006.01)
*A61B 17/70* (2006.01)

(52) U.S. Cl.
CPC ......... *A61B 17/7049* (2013.01); *A61B 17/7052* (2013.01)

(58) Field of Classification Search
CPC ........... A61B 17/7052; A61B 17/7049; A61B 17/705; A61B 17/7025
USPC .................................. 606/250–253, 276–279
See application file for complete search history.

(56) References Cited

U.S. PATENT DOCUMENTS

| | | | |
|---|---|---|---|
| 4,433,677 A | 2/1984 | Ulrich et al. | |
| 5,498,262 A | 3/1996 | Bryan | |
| 5,624,442 A | 4/1997 | Mellinger et al. | |
| 5,707,372 A | 1/1998 | Errico et al. | |
| 5,709,684 A | 1/1998 | Errico et al. | |
| 6,238,396 B1 * | 5/2001 | Lombardo | 606/86 A |
| 6,554,831 B1 | 4/2003 | Rivard et al. | |
| 7,645,294 B2 | 1/2010 | Kalfas et al. | |
| 7,722,645 B2 | 5/2010 | Bryan | |
| 7,744,633 B2 | 6/2010 | Berrevoets et al. | |
| 7,837,714 B2 * | 11/2010 | Drewry et al. | 606/250 |
| 2004/0010253 A1 * | 1/2004 | Morrison | 606/61 |
| 2004/0116928 A1 | 6/2004 | Young et al. | |
| 2005/0113831 A1 | 5/2005 | Franck et al. | |
| 2005/0228377 A1 | 10/2005 | Chao et al. | |
| 2006/0064092 A1 | 3/2006 | Howland | |
| 2006/0161154 A1 | 7/2006 | McAfee | |
| 2006/0189983 A1 | 8/2006 | Fallin et al. | |
| 2006/0195095 A1 | 8/2006 | Mueller et al. | |
| 2006/0217718 A1 | 9/2006 | Chervitz et al. | |
| 2006/0229616 A1 | 10/2006 | Albert et al. | |
| 2007/0055242 A1 | 3/2007 | Bailly | |
| 2007/0083201 A1 | 4/2007 | Jones et al. | |
| 2007/0270809 A1 | 11/2007 | Drewry et al. | |
| 2008/0243185 A1 | 10/2008 | Felix et al. | |
| 2009/0018586 A1 | 1/2009 | Butler et al. | |
| 2009/0093848 A1 * | 4/2009 | Neary et al. | 606/277 |
| 2009/0177234 A1 | 7/2009 | Butler et al. | |
| 2009/0234390 A1 | 9/2009 | Poirier et al. | |
| 2009/0326588 A1 * | 12/2009 | Felix et al. | 606/277 |
| 2010/0204733 A1 | 8/2010 | Rathbun et al. | |
| 2010/0249842 A1 | 9/2010 | Mir | |
| 2011/0152934 A1 * | 6/2011 | Asaad | 606/250 |

* cited by examiner

*Primary Examiner* — Mary Hoffman
*Assistant Examiner* — Tara R Carter
(74) *Attorney, Agent, or Firm* — David L. King

(57) ABSTRACT

A transverse crosslink device is presented. The transverse crosslink device has a connecting member, a first rod gripping assembly, and a second rod gripping assembly. The rod gripping assemblies can be pivotly connected to an end of the connecting member, such that the rod gripping assembly can selectively pivot in a direction substantially transverse to the longitudinal axis of the connecting member. The rod gripping assemblies can also be configured to selectively grip a portion of a stabilizer rod.

12 Claims, 8 Drawing Sheets

TRANSVERSE CROSSLINK DEVICE

FIELD OF THE INVENTION

Presented herein is a transverse crosslink device. More specifically, a mechanical cross-link device for use with dual rod orthopedic implant apparatus is presented.

BACKGROUND OF THE INVENTION

The spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this relative immobilization by implanting artificial assemblies in or on the spinal column.

A variety of systems have been disclosed in the art which achieve this immobilization by implanting artificial assemblies in, or on, the spinal column. These assemblies may be classified by their position relative to the spine, as anterior, posterior, or lateral implants. Anterior and lateral assemblies generally comprise short structures which support only a few adjacent vertebral bodies. Conversely, posterior implants often comprise pairs of elongate vertically aligned rods for stabilizing both short and long segments of the spine. Such posterior rods are coupled to the back of the spinal column via hooks which slip under the lamina, means for attaching to the transverse process, and/or by screws which are inserted through the pedicle bone. In order to provide enhanced torsional rigidity, these apparatus generally include cross-linking devices which couple the rods together transverse to the axis (vertical axis) of the apparatus.

SUMMARY

Presented herein is a transverse crosslink device for connecting substantially parallel rods in a bone screw assembly. The device comprises a connecting member, a first rod gripping assembly, and a second rod gripping assembly.

In one aspect the rod gripping assemblies are pivotly connected to an end of the connecting member, such that the rod gripping assembly can selectively pivot in a direction substantially transverse to the longitudinal axis of the connecting member. In another aspect, the rod gripping assemblies are configured to selectively grip a portion of a stabilizer rod.

In yet another aspect, the connection between the ends of the connecting member and the rod gripping assemblies can be telescoping, thereby permitting the rod gripping assemblies to selectively move in a longitudinal direction with respect to the connecting member. In one aspect, the length of the connecting member is selectively variable and can be adjusted before or during surgery. In still another aspect, the connecting member is substantially arcuate. This shape allows for clearance of crucial anatomy, such as the spinal cord.

Other aspects and embodiments of the transverse crosslink device are described herein. This description is meant to fully describe the transverse crosslink device, but not limit its design, function, or application.

BRIEF DESCRIPTION OF THE DRAWINGS

These and other features of the preferred embodiments of the present invention will become more apparent in the detailed description in which reference is made to the appended drawings wherein.

DETAILED DESCRIPTION OF THE INVENTION

Figure 1:
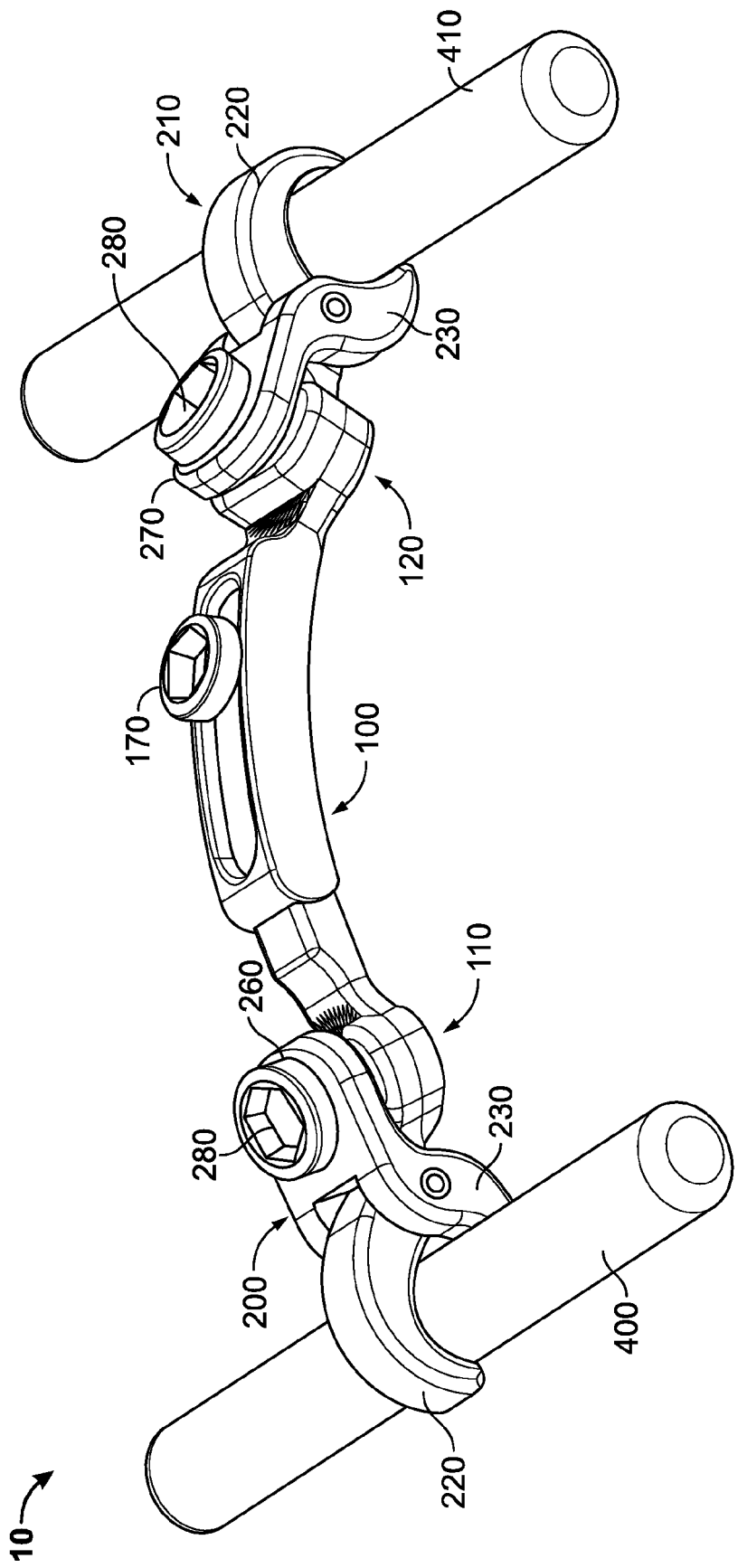
FIG. 1 is a perspective view of one aspect of a transverse crosslink device showing a first and second stabilizer rod in engagement with the crosslink device.
Figure 2:
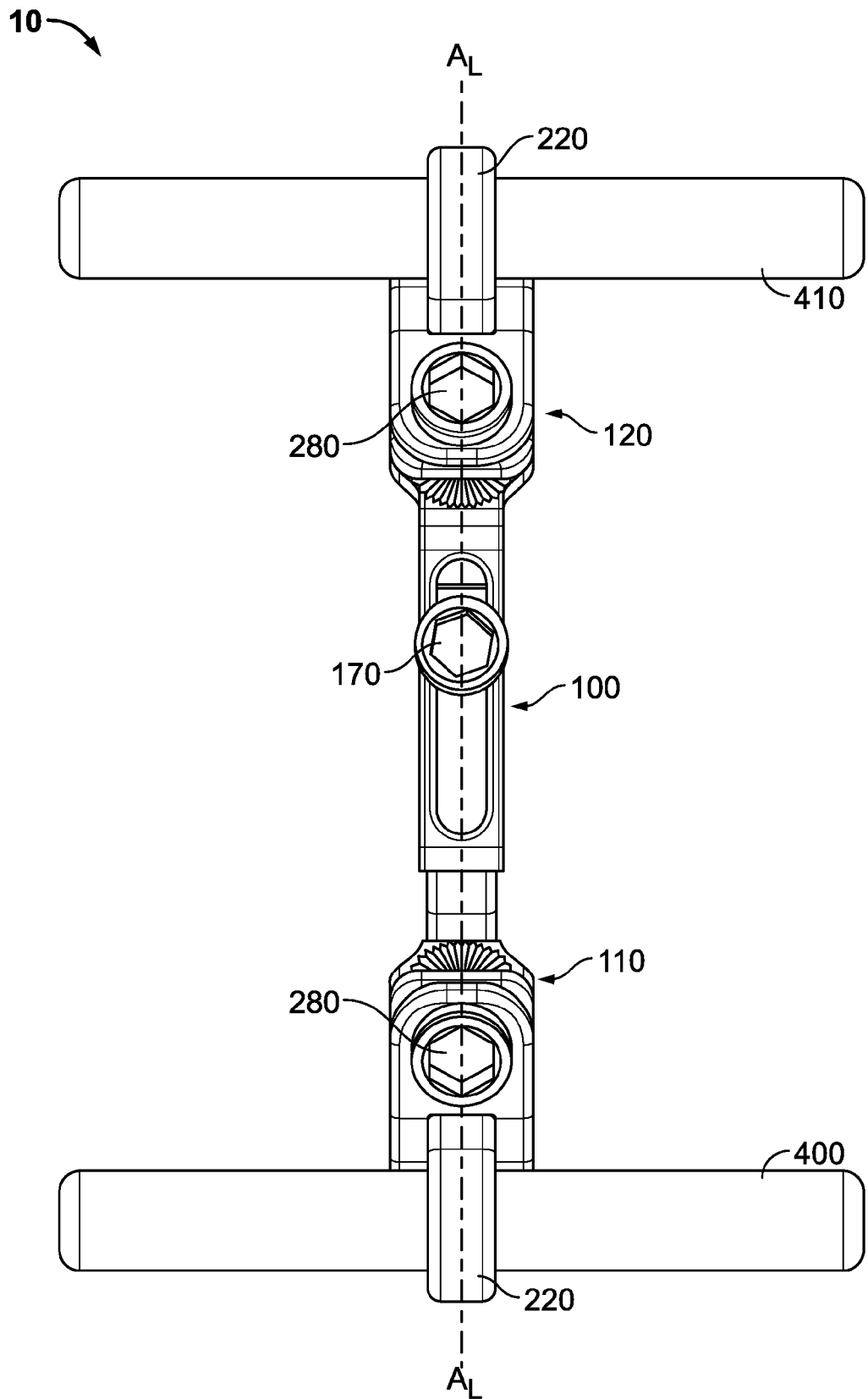
FIG. 2 is a top plan view of the crosslink device of FIG. 1.

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a rod" can include two or more such rods unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Presented herein is a transverse crosslink device 10 for connecting substantially parallel rods in a bone screw assembly. The device comprises a connecting member 100, a first rod gripping assembly 200, and a second rod gripping assembly 210.

In one aspect the first rod gripping assembly 200 is pivotly connected to the first end 110 of the connecting member 100, such that the first rod gripping assembly can selectively pivot in a direction substantially transverse to the longitudinal axis $A_L$ of the connecting member. The first rod gripping assembly is configured to selectively attach to a first stabilizing rod.

In another aspect, the second rod gripping assembly 210 pivotly connected to the second end 120 of the connecting member, such that the second rod gripping assembly can selectively pivot in a direction substantially transverse to the longitudinal axis of the connecting member. The second rod gripping assembly is configured to selectively attach to a second stabilizing rod 410.

As can be appreciated, the rod gripping assemblies are configured to selectively grip a portion of a stabilizer rod. As such, the first and second rod gripping assemblies each comprise a first jaw member 220 and a second jaw member 230 that are designed to selectively grip and release the respective stabilizer bar. In one aspect, the first and second jaw members each define a jaw cavity 240 therebetween and are configured to move from a first open position in which a respective stabilizer rod can ingress and egress the jaw cavity 240, and a second closed position in which the respective stabilizer rod is substantially maintained within the jaw cavity.

As best shown in FIG. 1, in one aspect, the first jaw member 220 and second jaw member 230 are pivotally connected. Of course, there are several ways in which to pivotally connect the two jaws. In the exemplified aspect shown, each jaw defines a pivot aperture 250 in which a pivot pin can reside. In this aspect, the first and second jaw members move from the first position to the second position in a scissor-like manner, meaning separation of the proximal portions of the first and second jaw members separates the distal portions of the jaw members, and vice-versa. The scissor clamping design creates less stress on the rod than traditional clamps with set screws. This design also allows for top-loading of the implant for easy installation.

In one exemplified aspect, the proximal portion 260 of the first jaw member 220 of the first rod gripping assembly is pivotally connected to the first end 110 of the connecting member 100 and a proximal portion 270 of the second jaw member 230 of the first rod gripping assembly 200 is connected to the proximal portion 260 of the first jaw member such that it can pivot therewith. This allows for alignment to rods that are not parallel to one another. In one aspect, the proximal portion of each jaw member defines an aperture 290 through which a fastener 280 can be positioned. The apertures of the first and second jaw members are substantially coaxial, such that tightening of the fastener 280 draws the proximal end of the second jaw member closer to the proximal end of the first jaw member. In this aspect, the first jaw member is substantially adjacent the first end of the connecting member. As can be appreciated by those skilled in the art, when the fastener is loose, the first rod gripping assembly is free to rotate about it. In this configuration, tightening of one fastener both tightens the rod gripping assembly and fixes the rotational position of the rod gripping assembly with respect to the connecting member. The second rod gripping assembly 210 can be configured in the same fashion, as well.

In this aspect, the bottom face of the proximal portion of the first jaw member 220 of the first rod gripping assembly comprises a plurality of radial teeth and a top face of the first end of the connecting member 100 comprises complimentary radial teeth. As such, tightening of the fastener 280 substantially compresses the proximal portion 260 of the first jaw member with the first end of the connecting member, which engages the radial teeth of the connecting member with the radial teeth of the proximal portion of the first jaw member. When the radial teeth of the connecting member and the radial teeth of the proximal portion of the first jaw member are engaged, the engagement substantially restricts rotation of the first rod gripping assembly with respect to the connecting member 100. As can be appreciated, the second rod gripping assembly and the second end 120 of the connecting member can be configured in the same fashion.

Figure 11:
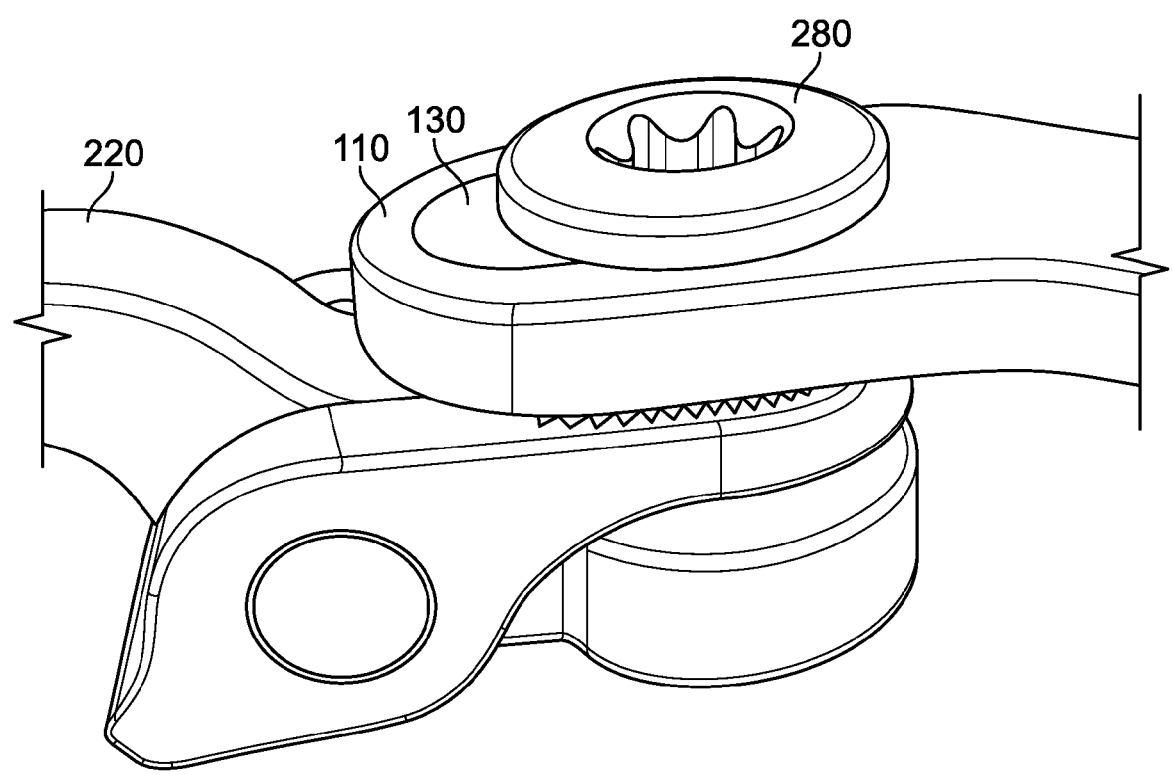
FIG. 11 is a perspective view of a rod gripping assembly connected to an end of a connecting member, where the connecting member has an elongate aperture.

In an exemplified aspect, the connection between the second end of the connecting member and the second rod gripping assembly is telescoping, thereby permitting the second rod gripping assembly to selectively move in a longitudinal direction with respect to the connecting member. As best shown in FIG. 11, the first and/or the second end of the connecting member 100 can define an elongate aperture 130 through which the fastener connects the respective jaw member to the respective end of the connecting member. When the fastener is loose, it is free to move longitudinally within the elongate aperture 130. It is also contemplated that one or both of the apertures of the jaw members can also be elongate.

At times, it may be desirable to have the jaw members of a rod gripping assembly in the normally open position, such that the stabilizer rod can move into and out of the jaw cavity easily. In one aspect, the first rod gripping assembly 200 comprises a first bias member 320 to maintain the first and second jaw members of the first rod gripping device in a normally open position. In this aspect, the bias member 320 can be positioned therebetween the proximal end of the first jaw member 220 and the second jaw member 230 urging them apart. The configuration can be the same for the second rod gripping assembly 210, where the bias member would be the second bias member, if desired.

In other instances, it may be desirable to have the jaw members of a rod gripping assembly in the normally closed position, such that a spring force would have to be overcome to open the jaw members and insert the stabilizer rod. In this aspect, the first rod gripping assembly comprises a first bias member 320 to maintain the first and second jaw members of the first rod gripping device in a normally closed position. In this aspect, the bias member 320 can be positioned therebetween the proximal end of the first jaw member and the first end 110 of the connecting member, urging the proximal ends of the jaw members together. It is also contemplated that the bias member can be positioned therebetween the proximal end of the second jaw member and a head of the fastener 280. Either configuration can be the same for the second rod gripping assembly, if desired. The bias members can comprise a coil spring, a leaf spring, a wave washer, and the like. Biocompatible materials for the bias member should be used. In one aspect, the bias member can be, for example and not meant to be limiting, Nitinol.

Figure 3:
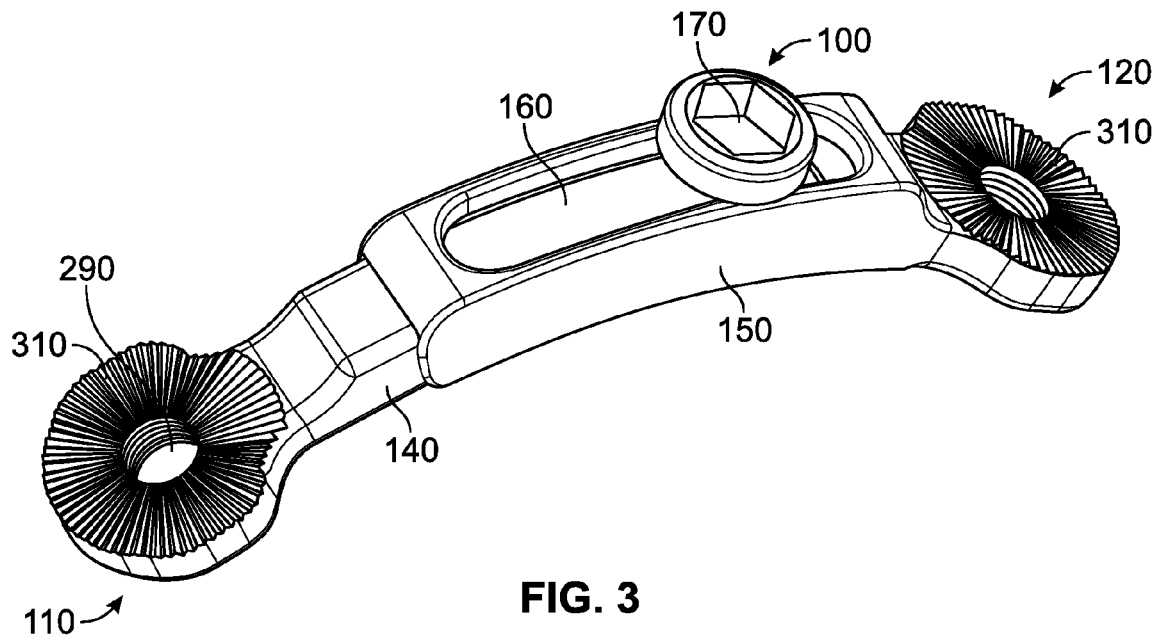
FIG. 3 is a perspective view of one aspect of a connecting member for use in a crosslink device.
Figure 4:
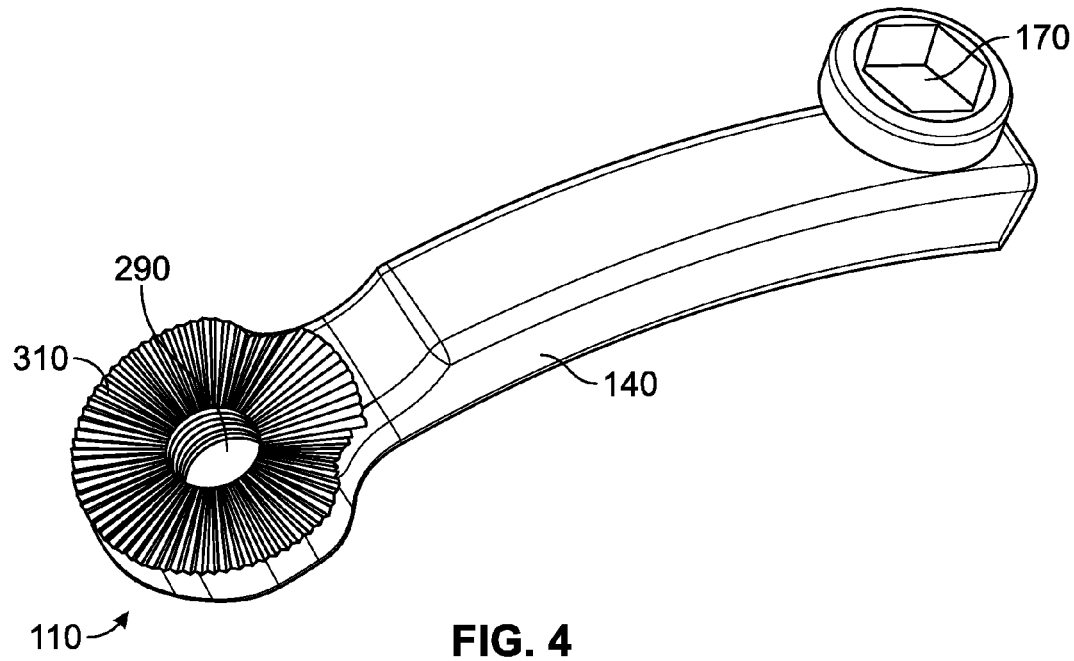
FIG. 4 is a perspective view of one aspect of a connecting rod for use with a crosslink device.
Figure 5:
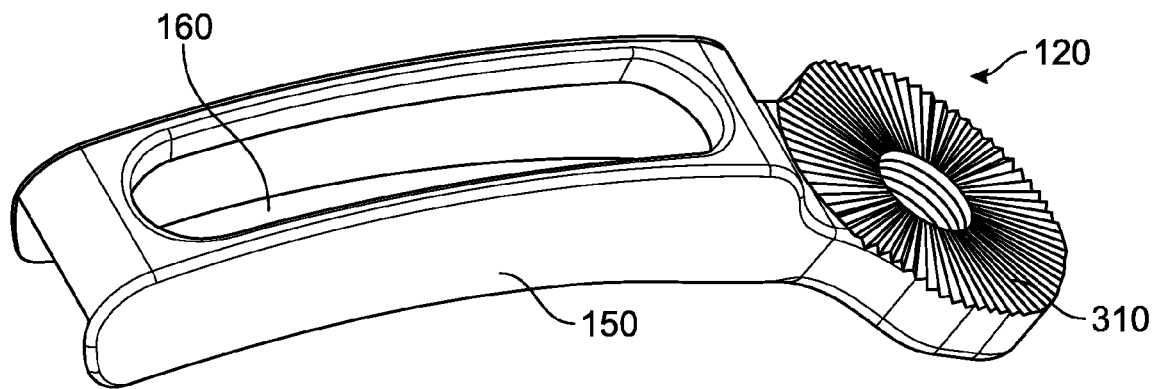
FIG. 5 is a perspective view of one aspect of a sleeve for use with the connecting rod of FIG. 4.
Figure 6:
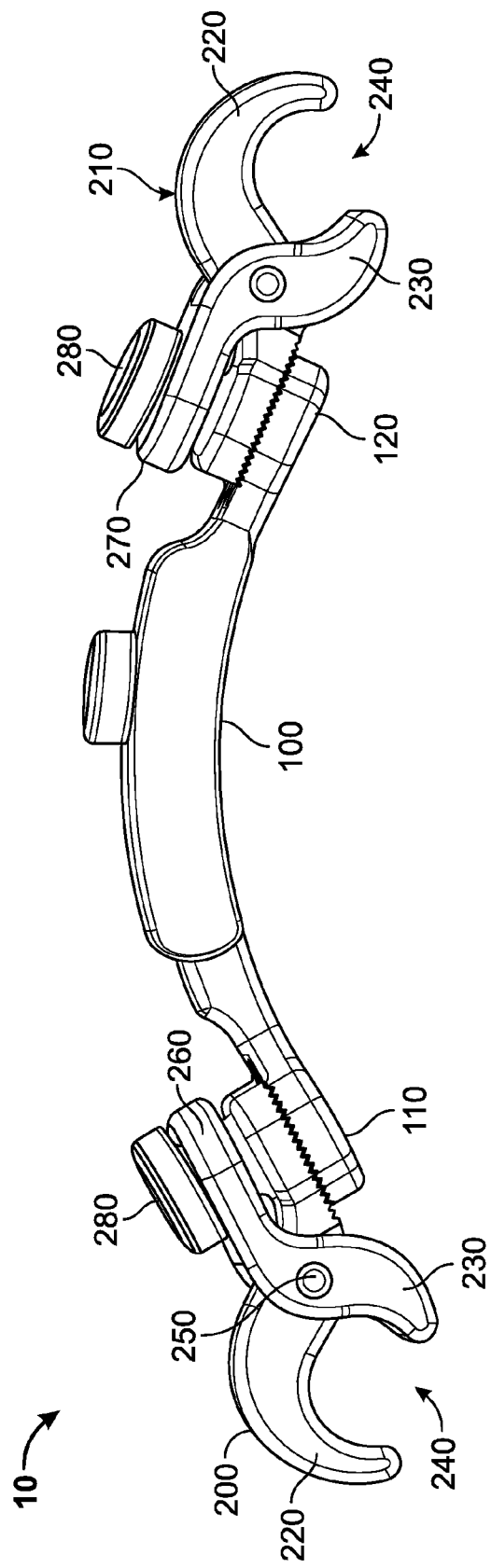
FIG. 6 is a side elevational view of the crosslink device of FIG. 1.
Figure 7:
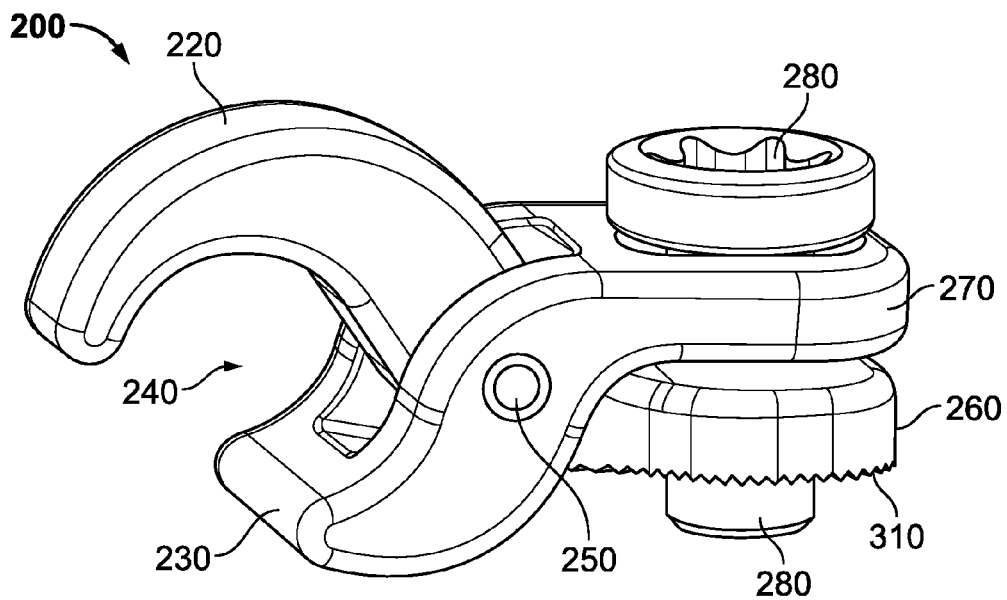
FIG. 7 is a perspective view of one aspect of a rod gripping assembly for use with a crosslink device.
Figure 8:
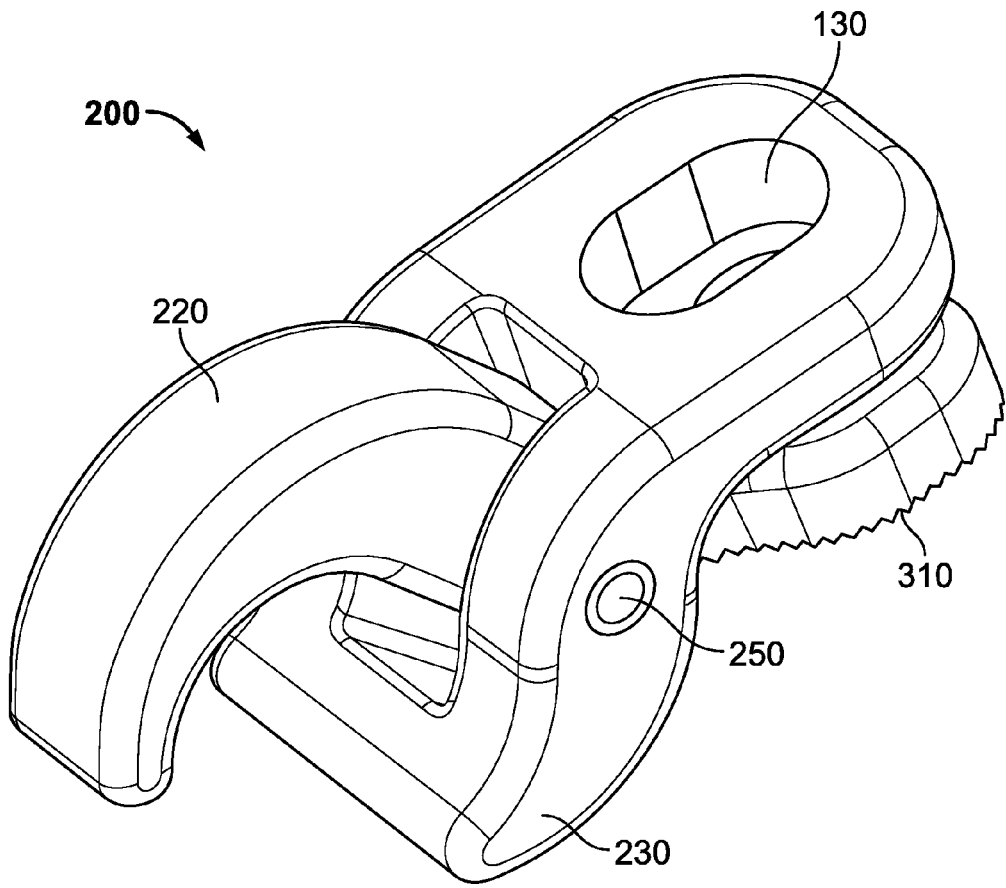
FIG. 8 is a perspective view of the rod gripping assembly of FIG. 7, showing an elongate aperture.
Figure 9:
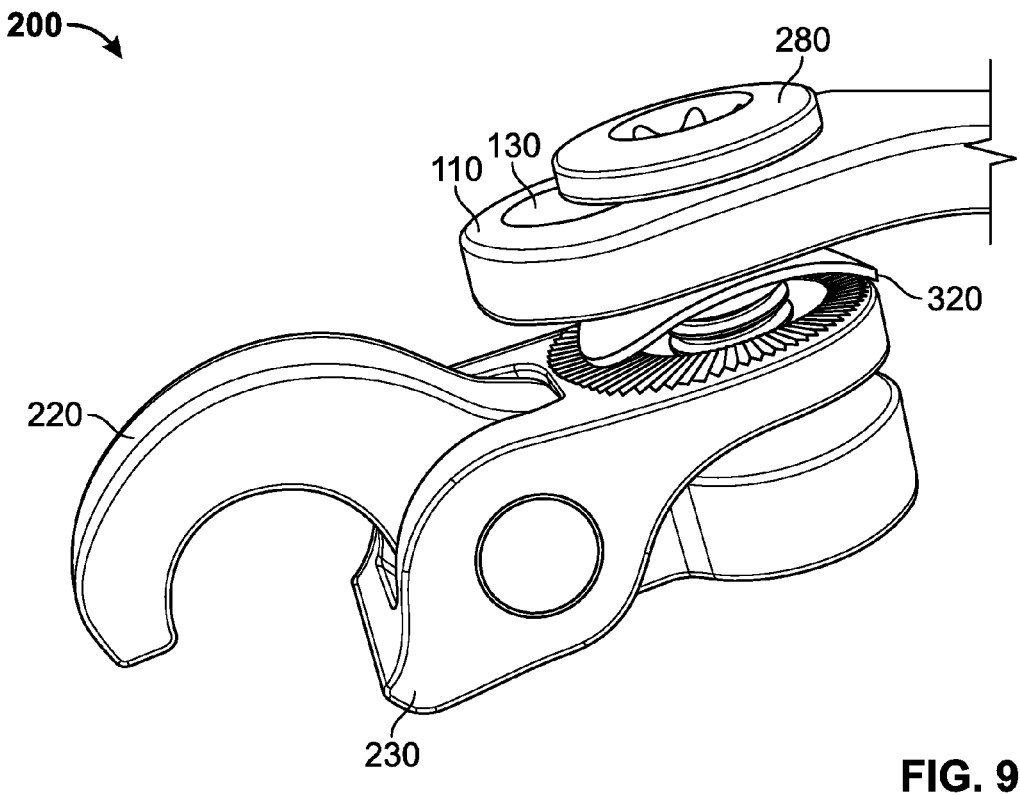
FIG. 9 is a perspective view of one aspect of a rod gripping assembly having a bias member to maintain the jaw members in a normally closed position.
Figure 10:
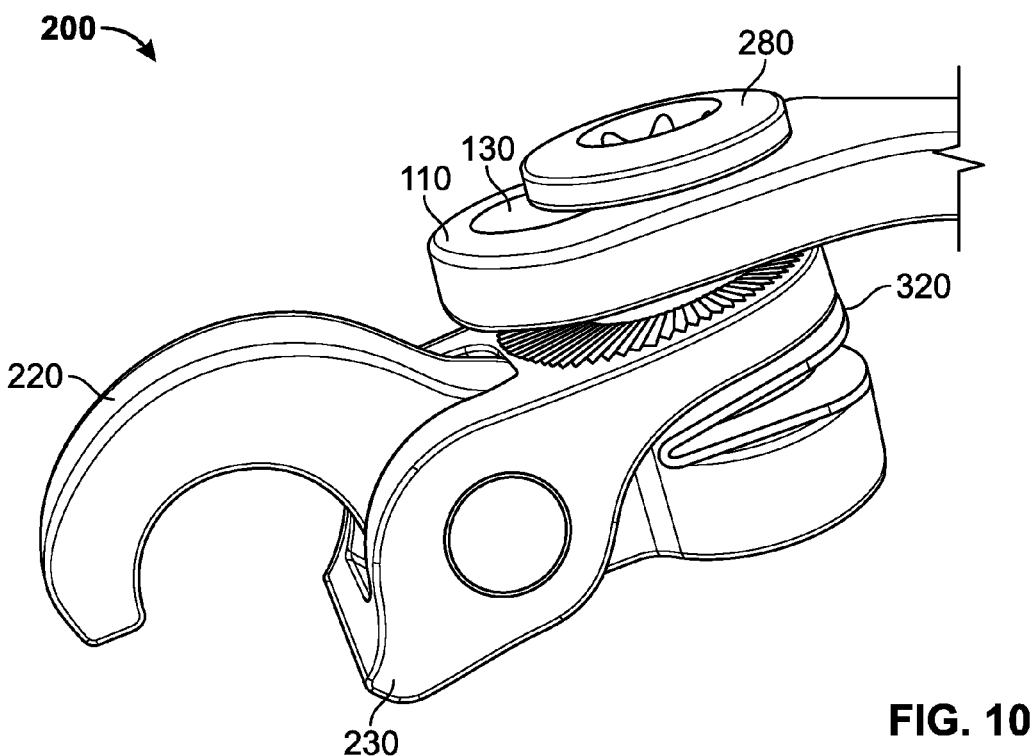
FIG. 10 is a perspective view of one aspect of a rod gripping assembly having a bias member to maintain the jaw members in a normally open position.

Since the anatomies of patients differ, it may be desirable to vary the length of the connecting member. In one aspect, the length of the connecting member is selectively variable and can be adjusted before or during surgery. In one such aspect, the connecting member 100 comprises a connecting rod 140 and a sleeve 150. In this aspect, the sleeve 150 defines a longitudinal sleeve cavity 160 and the rod is configured to at least partially slide within the longitudinal sleeve cavity 160 and be selectively retained therein. As shown in FIG. 3, there can be a set screw 170 positioned to frictionally engage the rod and retain its position within the sleeve. As one skilled in the art can appreciate, other manners to vary the length of the connecting member are contemplated and can be employed.

In still another aspect, the connecting member is substantially arcuate. This shape allows for clearance of crucial anatomy, such as the spinal cord.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

I claim:

1. A transverse crosslink device for connecting substantially parallel rods in a bone screw assembly, comprising:
   an arcuate connecting member having an arcuate or curved longitudinal axis, a variable adjustable length, a first arcuate rod end and a second arcuate sleeve end; a first rod gripping assembly pivotally connected to the first arcuate rod end of the connecting member, whereby the first rod gripping assembly can selectively rotate about said first arcuate rod end and can pivot in a direction substantially transverse to the arcuate or curved longitudinal axis of the connecting member, the first rod gripping assembly configured to selectively attach to a first stabilizing rod;
   a second rod gripping assembly pivotally connected to the second arcuate sleeve end of the connecting member, whereby the second rod gripping assembly can selectively rotate about said second arcuate sleeve end and pivot in a direction substantially transverse to the longitudinal axis of the connecting member, the second rod gripping assembly configured to selectively attach to a second stabilizing rod; wherein the first and second rod gripping assemblies each comprise a first jaw member and a second jaw member, each jaw member having a pivot aperture for receiving a pivot pin, the first and second jaw members defining a jaw cavity therebetween and are configured to move from an first open position in which a respective stabilizer rod can ingress and egress the jaw cavity, and a second closed position in which the respective stabilizer rod is substantially maintained within the jaw cavity and wherein the first and second jaw members are pivotally connected to permit the first and second jaw members to pivot about said pin to move from the first position to the second position in a scissor-like manner wherein the arcuate connecting member has the first arcuate rod end retained inside the second arcuate sleeve end such that the second arcuate sleeve end encircles the first arcuate rod and, wherein the second arcuate sleeve end defines a longitudinal curved sleeve cavity with a horizontal longitudinal axis such that the length of the connecting member is adjustable along the arcuate longitudinal axis of the connecting member wherein the first arcuate rod end is inside the arcuate sleeve cavity of the second arcuate sleeve end of the connecting member configured to slide co-axially telescoping to allow a length of the connecting member to be selectively variable and adjustable when the first arcuate rod end is selectively retained inside the arcuate sleeve cavity of the second arcuate sleeve end by a set screw positioned to frictionally engage the first arcuate rod end to retain the first arcuate rod end position within the second arcuate sleeve end.

2. The transverse crosslink device of claim 1, wherein a proximal portion of the first jaw member of the second rod gripping assembly is pivotally connected to the second end of the connecting member and a proximal portion of the second jaw member of the second rod gripping assembly is connected to the proximal portion of the first jaw member of the second rod gripping assembly such that it can pivot therewith.

3. The transverse crosslink device of claim 2, wherein a bottom face of the proximal portion of the first jaw member of the second rod gripping assembly comprises a plurality of radial teeth and a top face of the second end of the connecting member comprises complimentary radial teeth.

4. The transverse crosslink device of claim 3, further comprising a means for compressing the proximal portion of the first jaw member of the second rod gripping assembly with the second end of the connecting member, substantially engaging the radial teeth of the connecting member with the radial teeth of the proximal portion of the first jaw member of the second rod gripping assembly, thereby substantially restricting rotation of the second rod gripping assembly with respect to the connecting member.

5. The transverse crosslink device of claim 1, whereby the connection between the first end of the connecting member and the first rod gripping assembly is telescoping, thereby permitting the first rod gripping assembly to selectively move in a longitudinal direction with respect to the connecting member.

6. The transverse crosslink device of claim 1, whereby the connection between the second end of the connecting member and the second rod gripping assembly is telescoping, thereby permitting the second rod gripping assembly to selectively move in a longitudinal direction with respect to the connecting member.

7. The transverse crosslink device of claim 1, wherein the first rod gripping assembly comprises a first bias member to maintain the first and second jaw members of the first rod gripping device in a normally open position.

8. The transverse crosslink device of claim 1, wherein the first rod gripping assembly comprises a first bias member to maintain the first and second jaw members of the first rod gripping device in a normally closed position.

9. The transverse crosslink device of claim 1, wherein the second rod gripping assembly comprises a second bias member to maintain the first and second jaw members of the second rod gripping device in a normally open position.

10. The transverse crosslink device of claim 1, wherein the second rod gripping assembly comprises a second bias member to maintain the first and second jaw members of the second rod gripping device in a normally closed position.

11. A transverse crosslink device for connecting substantially parallel rods in a bone screw assembly, comprising:
   an arcuate connecting member having an arcuate or curved longitudinal axis, a variable adjustable length, a first arcuate rod end and a second arcuate sleeve end; a first rod gripping assembly pivotally connected to the first arcuate rod end of the connecting member, whereby the first rod gripping assembly can selectively rotate about said first arcuate rod end and can pivot in a direction substantially transverse to the arcuate or curved longitudinal axis of the connecting member, the first rod gripping assembly configured to selectively attach to a first stabilizing rod;
   a second rod gripping assembly pivotally connected to the second arcuate sleeve end of the connecting member, whereby the second rod gripping assembly can selectively rotate about said second arcuate sleeve end and pivot in a direction substantially transverse to the longitudinal axis of the connecting member, the second rod gripping assembly configured to selectively attach to a second stabilizing rod; wherein the first and second rod gripping assemblies each comprise a first jaw member and a second jaw member, each jaw member having a pivot aperture for receiving a pivot pin, the first and second jaw members defining a jaw cavity therebetween and are configured to move from an first open position in which a respective stabilizer rod can ingress and egress the jaw cavity, and a second closed position in which the respective stabilizer rod is substantially maintained within the jaw cavity and wherein the first and second jaw members are pivotally connected to permit the first and second jaw members to pivot about said pin to move from the first position to the second position in a scissor-like manner wherein the arcuate connecting member has the first arcuate rod end retained inside the second arcuate sleeve end such that the second arcuate sleeve end encircles the first arcuate rod and, wherein the second arcuate sleeve end defines a longitudinal curved sleeve cavity with a horizontal longitudinal axis such that the length of the connecting member is adjustable along the arcuate longitudinal axis of the connecting member wherein the first arcuate rod end is inside the arcuate sleeve cavity of the second arcuate sleeve end of the connecting member configured to slide co-axially telescoping to allow a length of the connecting member to be selectively variable and adjustable when the first arcuate rod end is selectively retained inside the arcuate sleeve cavity of the second arcuate sleeve end by a set screw positioned to frictionally engage the first arcuate rod end to retain the first arcuate rod end position within the second arcuate sleeve end, wherein a proximal portion of the first jaw member of the first rod gripping assembly is pivotally connected to the first end of the connecting member and a proximal portion of the second jaw member of the first rod gripping assembly is connected to the proximal portion of the first jaw member of the first rod gripping assembly such that it can pivot therewith and wherein a bottom face of the proximal portion of the first jaw member of the first rod gripping assembly comprises a plurality of radial teeth and a top face of the first end of the connecting member comprises complimentary radial teeth.

12. The transverse crosslink device of claim 11, further comprising a means for compressing the proximal portion of the first jaw member of the first rod gripping assembly with the first end of the connecting member, substantially engaging the radial teeth of the connecting member with the radial teeth of the proximal portion of the first jaw member of the first rod gripping assembly, thereby substantially restricting rotation of the first rod gripping assembly with respect to the connecting member.

* * * * *